US005128070A

United States Patent [19]

Sedelies et al.

[11] Patent Number: 5,128,070
[45] Date of Patent: Jul. 7, 1992

[54] PROCESS FOR THE ACID-CATALYZED CLEAVAGE OF FATTY ACID GLYCERIDES AND APPARATUS THEREFOR

[75] Inventors: Reinhold Sedelies, Ratingen; Wilhelm Johannisbauer, Erkrath; Guenter Wozny, Mettmann; Lutz Jeromin; Gerhard Dieckelm, both of Hilden; Manfred Lindemann, Solingen; Gerd Matrong, Duesseldorf, all of Fed. Rep. of Germany

[73] Assignee: Henkel Kommanditgesellschaft auf Aktien, Duesseldorf, Fed. Rep. of Germany

[21] Appl. No.: 388,206

[22] Filed: Aug. 1, 1989

[30] Foreign Application Priority Data

Aug. 1, 1988 [DE] Fed. Rep. of Germany ....... 3826119

[51] Int. Cl.⁵ ......................... C07C 27/02; C11C 1/06
[52] U.S. Cl. .................................... 554/160; 554/163
[58] Field of Search ................................ 260/415, 416

[56] References Cited

U.S. PATENT DOCUMENTS

| | | | |
|---|---|---|---|
| 601,603 | 3/1898 | Twitchell | 260/416 |
| 2,458,170 | 1/1949 | Ittner | 260/415 |
| 4,595,461 | 6/1986 | Jeromin et al. | 260/419 |

OTHER PUBLICATIONS

Vaidya et al., Chemical Abstracts vol. 66, 1967, Abstract 30232g.
Ullmann's Encyclopedia, 1976, pp. 529-548.
J. Am. Oil Chemists Soc., 1979, 729-732A.

*Primary Examiner*—Mukund J. Shah
*Assistant Examiner*—E. C. Ward
*Attorney, Agent, or Firm*—Ernest G. Szoke; Wayne C. Jaeschke; Henry E. Millson, Jr.

[57] ABSTRACT

Process for the acid-catalyzed hydrolysis of fatty acid glycerides, wherein the process is carried out continuously with the glyceride and the water being moved countercurrent to each other, and apparatus therefor.

18 Claims, 1 Drawing Sheet

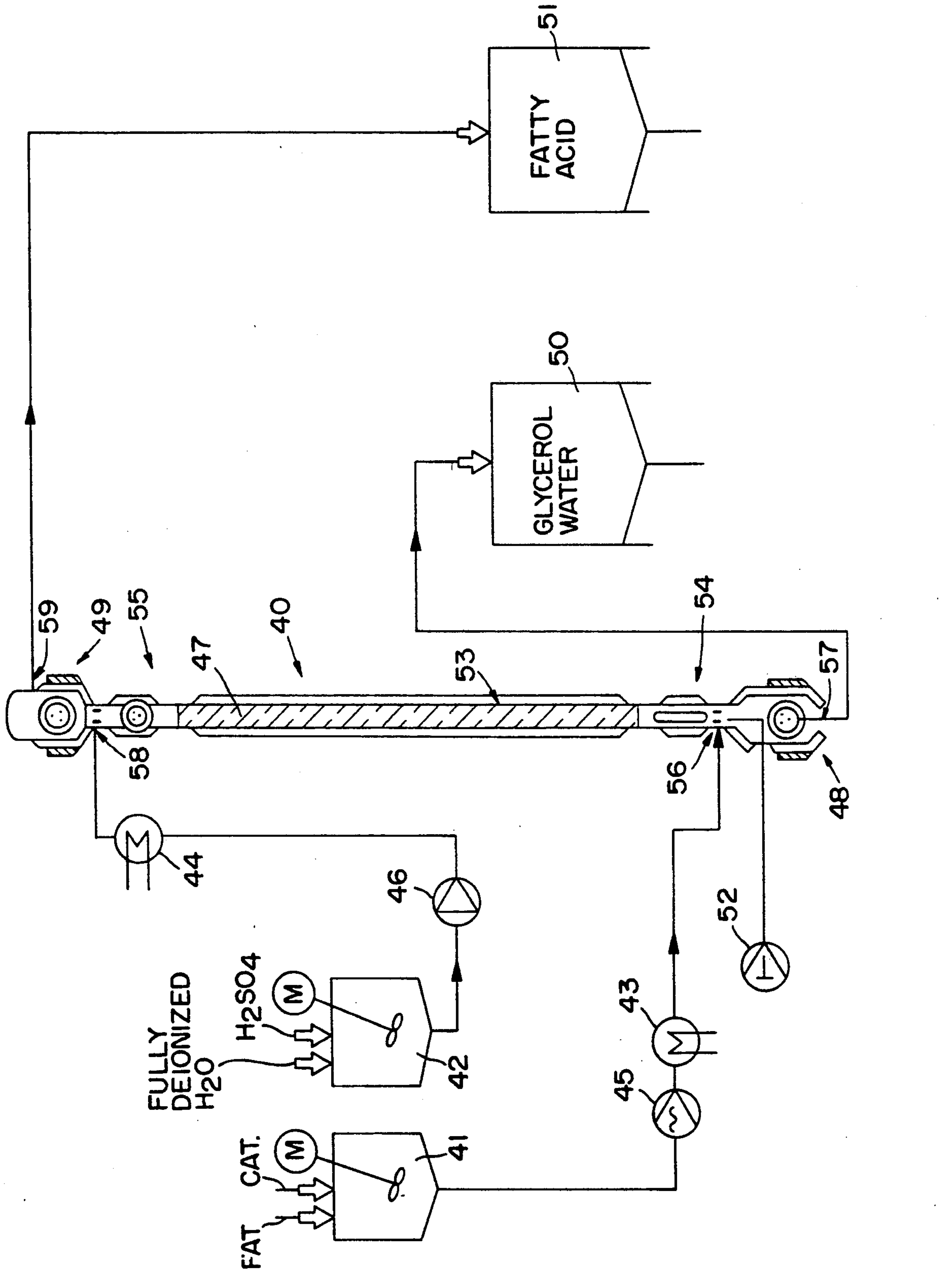
FATTY ACID
51
GLYCEROL WATER
50
59
49
55
47
40
53
54
57
58
56
48
44
46
52
43
45
42
41
FULLY DEIONIZED H2O
H2SO4
M
CAT.
FAT

PROCESS FOR THE ACID-CATALYZED CLEAVAGE OF FATTY ACID GLYCERIDES AND APPARATUS THEREFOR

BACKGROUND OF THE INVENTION

1. Field of the Invention

This invention relates to a process and to apparatus for the acid-catalyzed hydrolysis of fatty acid glycerides.

2. Statement of Related Art

Processes are known to the art for the hydrolysis of fatty acid glycerides with water to fatty acids and glycerol. At the present time the typical commercial process is mainly carried out in the absence of a catalyst under pressures of from 20 to 60 bar and at temperatures in the range of from 150° to 260° C., and is therefore energy-intensive.

The reaction velocity can be increased by alkaline and acidic catalysts. However, the pressureless hydrolysis of glycerides is only possible with acidic catalysts by the so-called Twitchell process (Ullmann's Enzyklopädie der technischen Chemie, 4th Edition, Vol. 11, page 529, last paragraph). The acidic catalysts used for this process consist of aromatic sulfonic acids. Although the process can be carried out in the absence of pressure at temperatures of the order of 100° C., this does require very long reaction times of more than 20 hours. In addition, no continuous version of the process is known.

According to N.O.V. Sonntag in J. Am. Oil Chemists' Soc., 1979, 729 A, the Twitchell process is carried out in batches in three or four successive steps. Fresh water containing the catalyst is added in each step. The following times and yields are obtained, for example, in a four-step Twitchell process:

in the first step, 18 hours and 60%,
in the second step, 12 hours and 25%,
in the third step, 6 hours and 10% and
in the fourth step, 4 hours and 5%.

The following times and yields are obtained in a three-step process:

in the first step, 20 to 24 hours and 75%,
in the second step, 12 hours and 15% and
in the third step, 4 hours and 5%.

In another known acid-catalyzed process, hydrolysis is carried out in batches on an industrial scale in two stages. The yield is only 88–90%.

In the known processes, the degree of hydrolysis is never better than 95% except in cases of very long reaction times or a very large number of steps with increasingly lower concentrations of glycerol. For this reason, these known processes are also energy-intensive.

BRIEF DESCRIPTION OF THE DRAWING

The FIGURE sets forth schematically the apparatus advantageously employed in the process of the invention.

DESCRIPTION OF THE INVENTION

Other than in the operating examples and claims, or where otherwise indicated, all numbers expressing quantities of ingredients or reaction conditions used herein are to be understood as modified in all instances by the term "about".

Accordingly, the present invention was made to provide a more economical process than the known processes for the acid-catalyzed hydrolysis of fatty acid glycerides.

According to the invention, the above process is carried out continuously with the glyceride and the water being moved countercurrent to each other. It is thus possible to shorten the batch time and the reaction time and to considerably reduce the residence time and, at the same time, obtain fully continuous countercurrent operation. In terms of plant, this countercurrent principle can be put into practice in any of the countercurrent apparatus normally used for liquid-liquid extraction, such as stirred and pulsed columns, mixer-settlers, extraction columns with and without fittings, to name only the most important.

With the process of the invention, degrees of hydrolysis of more than 95% can be obtained in batch times of less than 10 hours in 2 to 3 stages, for example in the mixer settler described in the following.

It is known that aryl sulfonic acids are used as catalysts in the acid-catalyzed hydrolysis of fatty acid glycerides. According to one aspect of the present invention, a particularly good catalytic effect can be obtained by using as catalyst an alkyl benzenesulfonic acid of which the alkyl radical contains a number of carbon atoms differing by at most 2 from the average number of carbon atoms of the fatty acids in the glyceride to be hydrolyzed.

In numerous experiments, alkyl benzenesulfonic acids differing in the length of their alkyl chains were used as catalysts in the hydrolysis of fats. Fats having an average fatty acid chain length of 6 to 22 carbons atoms were hydrolyzed. Using an alkyl benzenesulfonic acid containing a $C_{18}$ alkyl radical, the highest reaction velocity was obtained under otherwise the same conditions in the case of tallow in which the fatty acids also have an average chain length of about 18 carbon atoms. By contrast, in the hydrolysis of palm kernel oil which has an average chain length of 12 to 13 carbon atoms, the highest reaction velocity constant was obtained with an alkyl benzenesulfonic acid containing a $C_{13}$ alkyl radical.

It is also possible to use a single arylsulfonic acid for all glycerides. In this case, the proposed catalyst is dodecyl benzenesulfonic acid because this acid has been found to be the best universal catalyst for the hydrolysis of glycerides and partial glycerides across the entire molecular weight spectrum. In every instance, a mineral acid also has to be added to the water as proton donor in the process of the invention. Concentrations of from 0.5 to 1.5% by weight are particularly economical. Sulfuric acid is advantageously used as the proton donor.

Particularly good results are obtained with the process of the invention where it is carried out at a temperature of at least 90° C. under an excess pressure of up to 5 bar abs. because, beyond that temperature, the reaction velocities are particularly high.

Any further increase in temperature, even beyond 100° C., reduces the reaction times to an even greater extent. In this case, however, the reaction has to be operated under slight excess pressure to ensure that the water used remains in the liquid state. However, the temperature should not be so high that low-pressure steam cannot still be used. Accordingly, in a particularly economic embodiment, the process according to the invention is carried out at a temperature in the range of from 90° to 135° C. and more especially at a temperature in the range of from 120° to 135° C.

It is also of advantage to control the input of energy into the reactor in such a way that the water is finely dispersed, but at the same time a stable emulsion is avoided. The fine dispersion increases the reaction velocity whereas a stable emulsion would delay separation of the aqueous phase on completion of the reaction.

Particularly good results are obtained where the glyceride phase and the water phase are alternately mixed and separated and, after separation, flow countercurrent to one another. This method of operation can be carried out, for example, in a multistage cascade of stirred tanks. To shorten the overall duration of the process, the shortest possible separation time in each stage is important in this case. In this embodiment of the process of the invention, the energy input into each reaction stage again has to be adjusted accordingly.

To work up the reaction products, the glycerol is separated off from the sour water and the crude fatty acid is distilled. The glycerol can be separated off by known processes, for example by lime-soda precipitation, purification, and concentration by evaporation. Distillation of the crude fatty acid is preferably carried out in the plant operation according to U.S. Pat. No. 4,595,461, which is incorporated herein by reference. However, the water content of the fatty phase has to be reduced before it enters the degasser of this plant. The water can be separated from the crude fatty acid immediately after hydrolysis. Alternatively, however, the water can also be separated off in separate apparatus, for example in a centrifuge or a separator.

Accordingly, to work up the reaction mixture by the process according to U.S. Pat. No. 4,595,461, the water phase and the fatty phase are separated from one another, in particular mechanically, before the fatty phase is degassed.

To increase the economy of the process as a whole, the fatty acid is separated from the crude fatty acid after hydrolysis, as described in U.S. Pat. No. 4,595,461, and the residue is recycled to the hydrolysis process. This residue essentially contains unreacted glycerides, catalyst and fatty acid, the catalyst being recovered and the yield of fatty acid increased by the recycling.

Tests have shown that, in the acidic hydrolysis of fats, there is no need to reprocess the residue which may be directly returned to the hydrolysis process. However, part of the residue, for example from 10 to 25%, has to be continuously removed from the circuit to prevent any accumulation of fat impurities.

The fatty acid is preferably separated from the crude fatty acid by the distillation process described, for example, in U.S. Pat. No. 4,595,461.

The present invention also relates to a plant and apparatus for the continuous, acid-catalyzed hydrolysis of fatty acid glycerides comprising a column tube — designed for water descending in countercurrent flow to ascending fat — of a hydrolysis column which comprises a fat inlet and a glycerol water outlet at its sump and a water inlet and fatty acid outlet at its head with a heating system and a delivery pump preceding the inlet and receivers following the outlets for glycerol-water, and fatty acid. To obtain pure end products, at least one settling zone is provided between the head and/or the sump of the column and each of the receivers.

This settling zone may be separated from the column tube although it is particularly simple and economical if at least one settling zone is formed by an extension of the column tube wherein this extension has a relatively large cross-section.

To obtain high degrees of hydrolysis, the column is designed in such a way that a residence time of 2 to 5 hours can be obtained for the fatty phase. In one particularly advantageous variant of the process, the column is provided with additional fittings so that, given the above residence times, a degree of hydrolysis of up to 99% can be obtained with a mass ratio of water to fat of between 0.4 and 0.7. In addition, a glycerol concentration in the outflowing water of more than 20% can be obtained in this way.

The effect of the additional fittings is that the water droplets descending through the hydrolysis column are permanently deflected, dispersed and recombined and that the fat ascending through the column is permanently mixed radially with the water droplets in the absence of longitudinal mixing. This better intermixing further increases the reaction velocity. It is also of advantage for the fittings to have a free volume of at least 90%. Suitable fittings are, for example, plates of different design and packings.

In order further to accelerate the permanent changing of the interface between the liquids, means for locally mixing the reactants without any axial back-mixing are associated directly or via the fittings with at least one of the two liquids moving in countercurrent. To this end, it is possible, for example, to use a sieve-plate column with moving fittings, a stirred column or many other types of columns and reactors.

The mixing effect can be obtained particularly easily by coupling a pulsation pump to the column.

Where the process according to U.S. Pat. No. 4,595,461 is used to work up the reaction mixture, it is important to bear in mind that, according to the present invention and in contrast to this prior art, the catalyst, namely the alkyl benzenesulfonic acid, is dissolved in the crude fatty acid in a concentration of less than 2% by weight. To ensure that this content of catalyst in the crude fatty acid is not decomposed during distillation of the fatty acid, the residence time of the liquid phase in the sump of the rectification column of the reprocessing plant should be as short as possible. Accordingly, where two falling film evaporators are used in the reprocessing section, particular design measures are taken to ensure that the sump section has a small volume for a large heating surface, no dead zones, etc.

In order to further reduce temperature stressing of the catalyst, the residue section of the rectification column is uncoupled from the retort and the falling film evaporator is operated under relatively low pressure. To do this in the reprocessing plant acording to DE-OS 33 22 535, the distillate is separately condensed and recycled, for example, to the feed stream.

Referring now to the Figure, the Figure shows a plant comprising a countercurrent column in which the process according to the invention can also be carried out. The column (40) having a head (55) and a sump (54) is fed from two reservoirs (41,42) with fat and catalyst on the one hand (41) and with fully deionized water and sulfuric acid on the other hand (42). From the reservoirs, the liquid is pumped by pumps (45,46) via heating systems (43, 44) to the head (58) and foot (56) of column 40. In column 40, the fatty phase is moved upwards countercurrent to the acidic aqueous phase. To obtain a longer residence time of the disperse phase, a larger interface and less axial backmixing (dispersion), column 40 contains packing (47). For the same reasons, the column of liquid in the column is vibrated by a pulsation pump (52). At the head and foot of the column, the tube cross-section (53) is widened to form settling zones (48,49). The products, namely glycerol-water, and fatty acid, are run off from these zones through outlets (57,59) into two reservoirs (50,51). Pump 52 is connected betwen the lower settling zone and the inlet for the fatty phase into the column.

With this plant, the necessary residence times for both phases are drastically reduced because the settling times are largely redundant. Good phase separation was obtained with this countercurrent column. Instead of a column packing, it would also be possible to use a plate column or an empty column or a loosely packed column. The effect of this plant in the settling zones is that the upper phase is a substantially water-free fatty phase while the lower glycerol water phase is substantially fat-free. In contrast to the mixer-settler unit, this column contains only reaction zones and no settling zones, so that the residence time in the column can be reduced to 2 to 5 hours in this plant. The column can be externally heated or directly steam-heated.

The continuous acid-catalyzed hydrolysis of fatty acid glycerides can be carried out not only in a column, but also in a multistage cascade of stirred tanks. Accordingly, the present invention also relates to a plant and apparatus for the continuous acid-catalyzed hydrolysis of fatty acid glycerides comprising at least one stirred tank with at least one fat inlet, at least one water inlet and at least one outlet. The inlets can all be preceded by at least one feed pump and at least one heating system. To enable continuous countercurrent operation to be obtained with this plant, so that the process described above can be carried out, the plant comprises several stirred tanks arranged one behind the other with settling tanks in between and is designed for countercurrent operation.

In a multistage cascade of stirred tanks such as this, countercurrent operation is made particularly simple by the provision of at least one outlet of the stirred tank and at least one opening in the upper wall section and at least one opening in the lower wall section of each settling tank.

In another advantageous embodiment, the plant is designed for a settling time in the settling tank of at least half an hour.

Several examples of this embodiment of the invention are described in detail in the following.

EXAMPLES

Example 1

The process according to the invention was carried out in a five-stage mixer-settler unit. The characteristic feature of this unit is that it was operated in countercurrent flow although it consisted of stirred tanks or vessels.

The fat and the catalyst were fed continuously into a stirred and heated receiver containing a level governor. From the receiver, the liquid was pumped via a heat exchanger into the first stirred tank of the steam-heated mixer-settler unit.

As in all embodiments, sulfuric acid was used as the proton-yielding acid. Fresh water and sulfuric acid were introduced into a second stirred and heated receiver provided with a level governor. From this receiver, liquid was continuously pumped via a heat exchanger to the last stirred tank of the mixer-settler unit. From the mixer-settler unit, glycerol water and fatty acid were diverted into further receivers.

The five-stage mixer-settler unit was operated with tallow and palm kernel oil with a ratio by weight of water to oil of 0.7. The process was safe for industrial operation over a wide range. The phases in the settler were separated relatively quickly where 1% by weight sulfuric acid and 1% by weight alkyl benzenesulfonic acid were used. A residence time of the glycerol water phase of half an hour in the settler was advantageous for complete separation of the fatty phase. There was no evidence of an emulsion having been formed either through the direct introduction of steam or through high stirrer speeds. The temperature was limited to 98.5° C. to avoid foaming and evaporation of the water of reaction.

With this five-stage unit, degrees of hydrolysis of more than 95% free fatty acid were obtained for long total residence times of the fatty phase of more than ten hours. With this unit, the mean residence time of the fatty phase in the mixer, i.e. the actual reaction time, makes up only about 40% of the total residence time. In the case of palm kernel oil, a pure reaction time of 4 hours at an operating temperature of 98.5° C. was necessary to obtain a degree of hydrolysis of 95% free fatty acids. However, somewhat longer times were found to be necessary for products having a longer average chain length and a higher percentage of unsaturated fatty acids.

Example 2

In this example, palm kernel oil was again hydrolyzed using the equipment described in Example 1 above. The ratio by weight of water to fat (oil) was 0.7. 20 Kg fat/h and 14 kg water/h were used for a total volume of the mixer-settler unit of 400 l. The temperature in each stage was 98° C., only the stirred tanks or stirred vessels being heated. However, since the settling tanks were directly connected to them and were heat-insulated, the liquid had only slightly lower temperatures there. The unit was operated on an open basis in the absence of pressure. 1% by weight dodecyl benzenesulfonic acid, based on the fatty phase, was added as catalyst. 1% by weight sulfuric acid was added to the hydrolysis water. For working up, the fatty acid was distilled and the residue, which consisted of non-hydrolyzed glycerides and the catalyst, was recycled to the unit. The glycerol water was treated by the conventional lime-soda process and then purified by ion exchange and distillation. In this example, a degree of hydrolysis of 95% was obtained.

Example 3

In another example, a column with a random packing of Pall rings was used in the equipment shown in the Figure. The column had a cross-section of 100 mm in the reactor and 300 mm in the settling zones. The height of the settling zones was 0.6 m for an overall column height of 12 m. Beef tallow was used as the fatty phase. The catalyst and proton donor used were the same as in Example 1 (1% by weight of each). The column was operated with a throughput of 27 kg/h for the fatty phase and 18 kg/h for the aqueous phase. The pulsation stroke was 10 mm for a pulsation frequency of 100/min. The column was operated at a temperature of 130° C. under a pressure of 3.5 bar absolute. A degree of hydrolysis of 97.5% and a glycerol concentration in the glycerol water of 14% by weight were obtained in this example.

Example 4

In another example, glycerides obtained from head-fractionated fatty acids were hydrolyzed in the same column and the same plant as in Example 3 above. A degree of hydrolysis of 98% and a glycerol concentration of 20% by weight in the glycerol water were obtained for throughputs of 24 kg/h fat and 24 kg/h water at a temperature of 130° C. and under a pressure of 3.5 bar absolute.

In this example also, the crude fatty acid was separated from the residue by distillation and returned to the plant. The glycerol water was treated by the conventional lime-soda process and then purified by ion exchange and partly by distillation.

Example 5

The effect which the number of carbon atoms in the alkyl radical of the alkyl benzenesulfonic acid (ABS) has on the reaction velocity of the acid-catalyzed hydrolysis of glycerides is demonstrated in the following. Calculation of the velocity constants was based on a first-order equilibrium reaction;

$$kt + b = ln(\epsilon_{\infty}/(\epsilon_{\infty} - \epsilon(t))) \text{ with } \epsilon = \frac{AN}{SN}$$

The average carbon chain length of the fatty acids in palm kernel oil is approximately 12 and, in tallow, approximately 18. The following Table shows the test results obtained with palm kernel oil and tallow in a 2-liter stirred tank:

TABLE

| Fat | $C_{ABS}$ | k (1/s) |
|---|---|---|
| Palm kernel oil | 11-12 | 0.840 |
| Palm kernel oil | 13.2 | 1.161 |
| Palm kernel oil | 9.6 | 0.892 |
| Palm kernel oil | 18 | 0.767 |
| Tallow | 11-12 | 0.594 |
| Tallow | 9.6 | 0.532 |
| Tallow | 13.2 | 0.552 |
| Tallow | 18 | 0.812 |

We claim:

1. In a process for the continuous acid-catalyzed hydrolysis of fatty acid glycerides, the improvement wherein the process is carried out so that the fatty acid glyceride and the water used for hydrolysis are moved countercurrent to each other and wherein the catalyst is an alkyl benzenesulfonic acid, the alkyl radical thereof having a number of carbon atoms differing by at most two from the average number of carbon atoms in the fatty acid moieties of the fatty acid glyceride to be hydrolyzed.

2. The process of claim 1 wherein said alkyl radical has about the same number of carbon atoms as the average number of carbon atoms in the fatty acid moieties of the fatty acid glyceride to be hydrolyzed.

3. The process of claim 1 wherein the catalyst is dodecyl benzenesulfonic acid.

4. The process of claim 1 wherein the process is carried out in batch reaction at a temperature in the range of from about 90° to about 150° C. and under an excess pressure of up to about 5 bar absolute.

5. The process of claim 1 wherein a mineral acid acting as proton donor is present in a concentration of from about 0.5 to about 1.5% by weight.

6. The process of claim 5 wherein the mineral acid is sulfuric acid.

7. The process of claim 1 wherein the process is carried out at a temperature of at least 90° C. and an excess pressure of up to 5 bar absolute.

8. The process of claim 7 wherein the temperature is in the range of from about 90° to about 150° C.

9. The process of claim 8 wherein the temperature is in the range of from about 90° to about 135° C.

10. The process of claim 8 wherein the temperature is in the range of from about 120° C. to about 135° C.

11. The process of claim 1 wherein the process is carried out so that the water is finely dispersed, but not in the form of a stable emulsion.

12. In a process for the continuous acid-catalyzed hydrolysis of fatty acid glycerides, the improvement wherein the process is carried out so that the fatty acid glyceride and the water used for hydrolysis are alternately mixed and separated, and after separation, flow countercurrent to each other, and wherein the catalyst is an alkyl benzenesulfonic acid, the alkyl radical thereof having a number of carbon atoms differing by at most two from the average number of carbon atoms in the fatty acid moieties of the fatty acid glyceride to be hydrolyzed.

13. In a process for the continuous acid-catalyzed hydrolysis of fatty acid glycerides, the improvement wherein the process is carried out so that the fatty acid glyceride and the water used for hydrolysis are moved countercurrent to each other; wherein the catalyst is an alkyl benzenesulfonic acid, the alkyl radical thereof having a number of carbon atoms differing by at most two from the average number of carbon atoms in the fatty acid moieties of the fatty acid glyceride to be hydrolyzed, and wherein the reaction mixture obtained from the process is separated into an aqueous phase and a fatty acid phase, and the fatty acid phase is then degassed.

14. In a process for the continuous acid-catalyzed hydrolysis of fatty acid glycerides, the improvement wherein the process is carried out so that the fatty acid glyceride and the water used for hydrolysis are alternately mixed and separated and after separation flow countercurrent to each other; the process is carried out at a temperature of at least about 90° C. and an excess pressure of up to 5 bar absolute; the process is carried out so that the water is finely dispersed but is not in the form of a stable emulsion; from about 0.5 to about 1.5% by weight of a mineral acid is present as a proton donor; and wherein the catalyst is an alkyl benzenesulfonic acid, the alkyl radical thereof having a number of carbon atoms differing by at most two from the average number of carbon atoms in the fatty acid moieties of the fatty acid glyceride to be hydrolyzed.

15. The process of claim 13 wherein following degassing of the fatty acid phase, purified fatty acid is iisolated from the fatty acid phase, and the residue resulting therefrom is returned to the hydrolysis process.

16. The process of claim 15 wherein isolation of purified fatty acid is carried out by distillation.

17. The process of claim 14 wherein the temperature is in the range of from about 90° to about 150° C., and the mineral acid is sulfuric acid.

18. The process of claim 19 wherein the temperature is in the range of from about 90° C. to about 135° C.

* * * * *